(12) United States Patent
Kammer et al.

(10) Patent No.: US 9,114,218 B2
(45) Date of Patent: Aug. 25, 2015

(54) OPEN ACCESS SLEEVE FOR HEATED FLUID UNITS

(71) Applicant: C Change Surgical LLC, St. Paul, MN (US)

(72) Inventors: Patrick Kammer, Greensboro, NC (US); Kevin Joseph Rackers, Summerfield, NC (US); Mark Martel, Belews Creek, NC (US); Todd Cassidy, Mocksville, NC (US)

( * ) Notice: Subject to any disclaimer, the term of this patent is extended or adjusted under 35 U.S.C. 154(b) by 0 days.

(21) Appl. No.: 13/887,604

(22) Filed: May 6, 2013

(65) Prior Publication Data

US 2013/0310799 A1 Nov. 21, 2013

Related U.S. Application Data

(62) Division of application No. 12/972,629, filed on Dec. 20, 2010, now Pat. No. 8,523,082, which is a division of application No. 11/378,531, filed on Mar. 17, 2006, now Pat. No. 7,854,387.

(51) Int. Cl.
| | |
|---|---|
| G05D 23/12 | (2006.01) |
| F27D 11/00 | (2006.01) |
| H05B 3/00 | (2006.01) |
| A61M 5/44 | (2006.01) |
| G05D 23/20 | (2006.01) |
| G05D 23/22 | (2006.01) |
| A61B 19/02 | (2006.01) |

(52) U.S. Cl.
CPC ........... *A61M 5/445* (2013.01); *G05D 23/2028* (2013.01); *G05D 23/2208* (2013.01); *A61B 2019/0298* (2013.01)

(58) Field of Classification Search
USPC ............... 236/1 C; 219/430, 433, 435, 438, 219/476–480; 604/114, 291
See application file for complete search history.

(56) References Cited

U.S. PATENT DOCUMENTS

| | | |
|---|---|---|
| 189,590 A | 4/1877 | Wright |
| 199,370 A | 1/1878 | Kearns |
| 255,165 A | 3/1882 | Hale |
| 269,054 A | 12/1882 | Hemsteger |
| 298,287 A | 5/1884 | Cochran et al. |
| 1,797,963 A | 3/1931 | Neller |

(Continued)

OTHER PUBLICATIONS

"Clinical Guideline for the Prevention of Unplanned Perioperative Hypothermia", American Society of PeriAnesthesia Nurses, 15 pgs., published approx. Oct. 2002, www.aspan.org.

(Continued)

*Primary Examiner* — Marc Norman
(74) *Attorney, Agent, or Firm* — Amy J. Hoffman

(57) ABSTRACT

A series of implementations of open access sleeves for holding one or more closed containers of sterile fluid for use in medical procedures are disclosed. The open access sleeves may be adapted to provide heat to maintain the containers of sterile fluid above the ambient air temperature of the room. The provision of heat may be controlled by a control system. The control system may use a temperature measurement device to obtain a temperature representative of the container of sterile fluid and of the sterile fluid in the container. The access sleeve may be included in a device for maintaining an open volume of sterile fluid within a range of a target temperature to maintain the closed containers of sterile fluid at a temperature near target temperature for open volume of sterile fluid.

8 Claims, 12 Drawing Sheets

(56) References Cited

U.S. PATENT DOCUMENTS

| | | | |
|---|---|---|---|
| 1,811,896 | A | 6/1931 | Ross |
| 2,682,602 | A | 6/1954 | Huck |
| 2,892,066 | A | 6/1959 | Springer |
| 2,994,761 | A | 8/1961 | Hart et al. |
| 3,031,565 | A | 4/1962 | Appleton et al. |
| 3,374,936 | A | 3/1968 | Colato |
| 3,698,594 | A | 10/1972 | Boehlert |
| 3,751,629 | A | 8/1973 | Eisler |
| 3,767,898 | A | 10/1973 | Wells et al. |
| 3,974,358 | A | 8/1976 | Goltsos |
| 4,419,568 | A | 12/1983 | Van Overloop |
| 4,700,050 | A | 10/1987 | Hennuy et al. |
| D298,452 | S | 11/1988 | Carter |
| 4,934,152 | A | 6/1990 | Templeton |
| 4,967,057 | A | 10/1990 | Bayless et al. |
| 4,967,061 | A | 10/1990 | Weber, Jr. et al. |
| 5,129,033 | A | 7/1992 | Ferrara et al. |
| 5,174,306 | A | 12/1992 | Marshall |
| 5,271,085 | A | 12/1993 | Carballo |
| 5,331,820 | A | 7/1994 | Faries, Jr. et al. |
| 5,400,616 | A | 3/1995 | Faries, Jr. et al. |
| 5,415,180 | A | 5/1995 | Horan |
| 5,435,322 | A | 7/1995 | Marshall |
| 5,451,747 | A | 9/1995 | Sullivan et al. |
| 5,551,240 | A | 9/1996 | Faries, Jr. et al. |
| 5,615,423 | A | 4/1997 | Faries, Jr. et al. |
| 5,653,938 | A | 8/1997 | Faries, Jr. et al. |
| 5,718,124 | A | 2/1998 | Senecal |
| 5,729,653 | A | 3/1998 | Magliochetti et al. |
| 5,862,672 | A | 1/1999 | Faries, Jr. et al. |
| 5,879,621 | A | 3/1999 | Faries, Jr. et al. |
| 6,091,058 | A | 7/2000 | Faries, Jr. et al. |
| 6,255,627 | B1 | 7/2001 | Faries, Jr. et al. |
| 6,259,067 | B1 | 7/2001 | Faries, Jr. et al. |
| 6,294,762 | B1 | 9/2001 | Faries, Jr. et al. |
| 6,342,691 | B1 | 1/2002 | Johnsgard et al. |
| 6,371,121 | B1 | 4/2002 | Faries, Jr. et al. |
| 6,384,380 | B1 | 5/2002 | Faries, Jr. et al. |
| 6,392,206 | B1 | 5/2002 | Von Arx et al. |
| 6,401,602 | B1 | 6/2002 | Lin |
| 6,417,498 | B1 | 7/2002 | Shields et al. |
| 6,433,317 | B1 | 8/2002 | Arx et al. |
| 6,457,601 | B1 | 10/2002 | Chappell |
| 6,660,974 | B2 | 12/2003 | Faries, Jr. et al. |
| 6,711,989 | B1 | 3/2004 | Sarnoff |
| 6,768,085 | B2 | 7/2004 | Faries, Jr. et al. |
| 6,860,271 | B2 | 3/2005 | Faries, Jr. et al. |
| 6,864,462 | B2 | 3/2005 | Sanoner et al. |
| 6,884,970 | B2 | 4/2005 | Lehman |
| 6,910,485 | B2 | 6/2005 | Faries, Jr. et al. |
| 6,918,395 | B2 | 7/2005 | Faries, Jr. et al. |
| 7,128,275 | B2 | 10/2006 | Kammer et al. |
| 7,176,030 | B2 | 2/2007 | Faries, Jr. et al. |
| D546,943 | S | 7/2007 | Kammer et al. |
| D546,944 | S | 7/2007 | Kammer et al. |
| D547,444 | S | 7/2007 | Kammer et al. |
| D568,989 | S | 5/2008 | Kammer et al. |
| D569,970 | S | 5/2008 | Kammer et al. |
| 2001/0045188 | A1 | 11/2001 | Tesngas |
| 2002/0043260 | A1 | 4/2002 | Layer et al. |
| 2002/0188259 | A1 | 12/2002 | Hickle et al. |
| 2003/0230588 | A1 | 12/2003 | Zepter |
| 2004/0065314 | A1 | 4/2004 | Layer et al. |
| 2005/0242086 | A1 | 11/2005 | Imura |
| 2005/0267425 | A1 | 12/2005 | Castora et al. |
| 2006/0011608 | A1 | 1/2006 | Lehman |
| 2006/0065276 | A1 | 3/2006 | Kammer et al. |
| 2006/0086361 | A1 | 4/2006 | Kammer et al. |
| 2011/0114629 | A1 | 5/2011 | Kammer et al. |

OTHER PUBLICATIONS

Sessler et al., "Nonpharmacological Prevention of Surgical Would Infections", Clinical Infectious Diseases, CID 2002:35 (Dec. 1) pp. 1397-1404. Published electronically Nov. 13, 2002 by Infectious Diseases Society of America.

OPEN ACCESS SLEEVE FOR HEATED FLUID UNITS

CROSS-REFERENCES TO RELATED APPLICATIONS

This application claims priority to U.S. patent application Ser. No. 13/972,629 for Open Access Sleeve for Heated Fluid Units filed Dec. 20, 2010, now allowed, which is a divisional application of U.S. Pat. No. 7,128,275 for Liquid Warming Device with Basin. The application claims priority to the priority applications for the '275 patent: A) U.S. Provisional Patent Application 60/603,957 for Heating Element for Liquid Warming Device filed Aug. 24, 2004; B) U.S. Provisional Patent Application 60/603,956 for Liquid Warming Device and Control System filed Aug. 24, 2004, and C) U.S. Design Pat. No. D547,444 filed Mar. 24, 2005 for Hospital Basin with Channel All four of these references are incorporated by reference herein.

FIELD OF THE INVENTION

This invention relates to improvements in methods and apparatus for heating of sterile surgical liquids. More specifically, this invention relates to devices used to keep sealed containers of sterile surgical liquids at or near a desired temperature above the ambient air temperature of the room. These devices may work in conjunction with another heating system to maintain an elevated temperature of surgical fluids in an open container such as a basin or cavity formed in a sterile drape.

BACKGROUND OF THE INVENTION

Devices for the heating of sterile surgical liquids are known in the art. In a wide variety of surgical procedures, sterile fluids are used to irrigate the site of the surgery. It is important that the temperature of the fluids used be strictly controlled. As the portion of the brain that regulates body temperature is shut down with anesthesia, it is important that the introduction of sterile fluids does not cool the body core temperature. Clinical studies have indicated that a range of adverse consequences arise from a change in body core temperature as little as one to three degrees Celsius. The adverse consequences from mild perioperative hypothermia include hypertension and increased vascular resistance, cardiac events, coagulopathy, an increase risk of surgical wound infections, and delays in the body's ability to remove drugs from its systems. An additional potential adverse consequence is shivering that may increase metabolic rate up to 500% and thus increase demands for oxygen and the need to clear carbon dioxide. This list of complications is by no means exhaustive, but it highlights the critical importance in controlling the body core temperature. Careful control of the temperature of sterile irrigation fluids is an important part of controlling body core temperature.

Co-pending and commonly assigned U.S. patent application Ser. No. 11/209,283 for Liquid Warming Device with Basin discloses various apparatus configurations and control schemes to precisely control the temperature of a sterile fluid in an open container such as a surgical basin or a surgical drape covering a cavity in a fluid warming device.

SUMMARY OF THE DISCLOSURE

The deficits in the prior art are addressed by the addition of one or more access sleeves to devices for maintaining open volumes of sterile fluid at an elevated temperature. Having access sleeves maintain or modify the temperature of sterile fluid in closed containers stored in the operating room allows the addition of sterile fluid from the closed containers to the open volume of heated sterile fluid without greatly changing the temperature of the new expanded volume of sterile fluid from a target temperature for the open volume of sterile fluid. While it may be convenient to have an access sleeve in the same device that maintains the open volume of sterile fluid at an elevated temperature, one or more access sleeves can be implemented in an access sleeve cabinet. The access sleeves may be implemented in a number of configurations. It may be useful to slope the access sleeve to allow fluids to drain out the open end of the access sleeve. It may be useful to slope the access sleeve so that containers tend to move to a particular portion of the access sleeve. If the access sleeve is sloped towards the open end, it may be useful to have protrusions that extend to impede the closed containers from slipping out of the open end of the access sleeve.

The access sleeve may be sized to receive more than one container of sterile fluid. The access sleeve may be configured to have two open ends so that containers of sterile fluid may be introduced or removed from either end.

The access sleeve may have heating elements that are controlled by a controller. The controller may act at least in part on a temperature measurement taken from a temperature sensing device adapted to obtain a temperature indicative of the temperature of the container of sterile fluid.

Temperature indicators may be provided that provide either a qualitative or quantitative indication of the temperature of the container of sterile fluid. The user may be allowed to alter the set point temperature for the control system to alter the target temperature for the closed container of sterile fluid. The A series of implementations of open access sleeves for holding one or more closed containers of sterile fluid for use in medical procedures are disclosed. The open access sleeves may be adapted to provide heat to maintain the containers of sterile fluid above the ambient air temperature of the room. The provision of heat may be controlled by a control system. The control system may use a temperature measurement device to obtain a temperature representative of the container of sterile fluid and of the sterile fluid in the container. The access sleeve may be included in a device for maintaining an open volume of sterile fluid within a range of a target temperature to maintain the closed containers of sterile fluid at a temperature near target temperature for open volume of sterile fluid.

Other systems, methods, features, and advantages of the invention will be or will become apparent to one with skill in the art upon examination of the following figures and detailed description. It is intended that all such additional systems, methods, features, and advantages be included within this description, be within the scope of this invention, and be protected by the accompanying claims.

BRIEF DESCRIPTION OF THE FIGURES

The invention can be better understood with reference to the following figures. The components of the figures are not necessarily to scale, emphasis being placed upon illustrating the principles of the invention. Moreover, in the figures, like reference numerals designate corresponding parts through the different views.

DETAILED DESCRIPTION

The present invention will now be described more fully hereinafter with reference to the accompanying drawings, in order to disclose selected embodiments. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
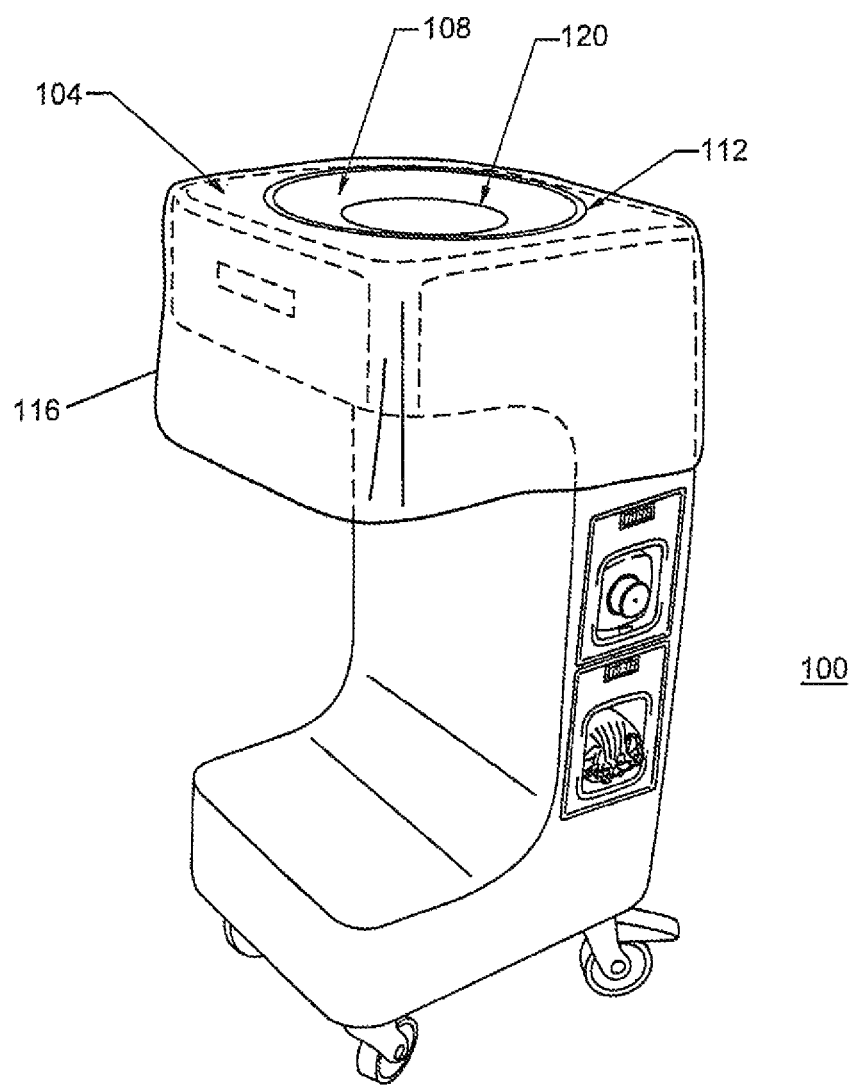
FIG. 1 is a perspective view of one implementation of a liquid warming device.

FIG. 1 is a perspective view of one implementation of a liquid warming device 100. The liquid warming device 100 has a top surface 104 adapted to receive a sterile removable basin 108 with a lip 112. The sterile removable basin 108 is combined with a sterile drape 116 with an opening so that the bottom of the sterile removable basin 108 extends through the opening in the sterile drape 116 to engage with the liquid warming device 100. Co-pending and commonly assigned U.S. patent application Ser. No. 11/209,283 for Liquid Warming Device with Basin (incorporated by reference above) describes desirable interactions between sterile removable basin 108 and the liquid warming device 100 to detect the presence of an appropriate sterile removable basin 108 and to sense the temperature of sterile fluid 120 through the use of a thermocouple well (not shown here).

Figure 2:
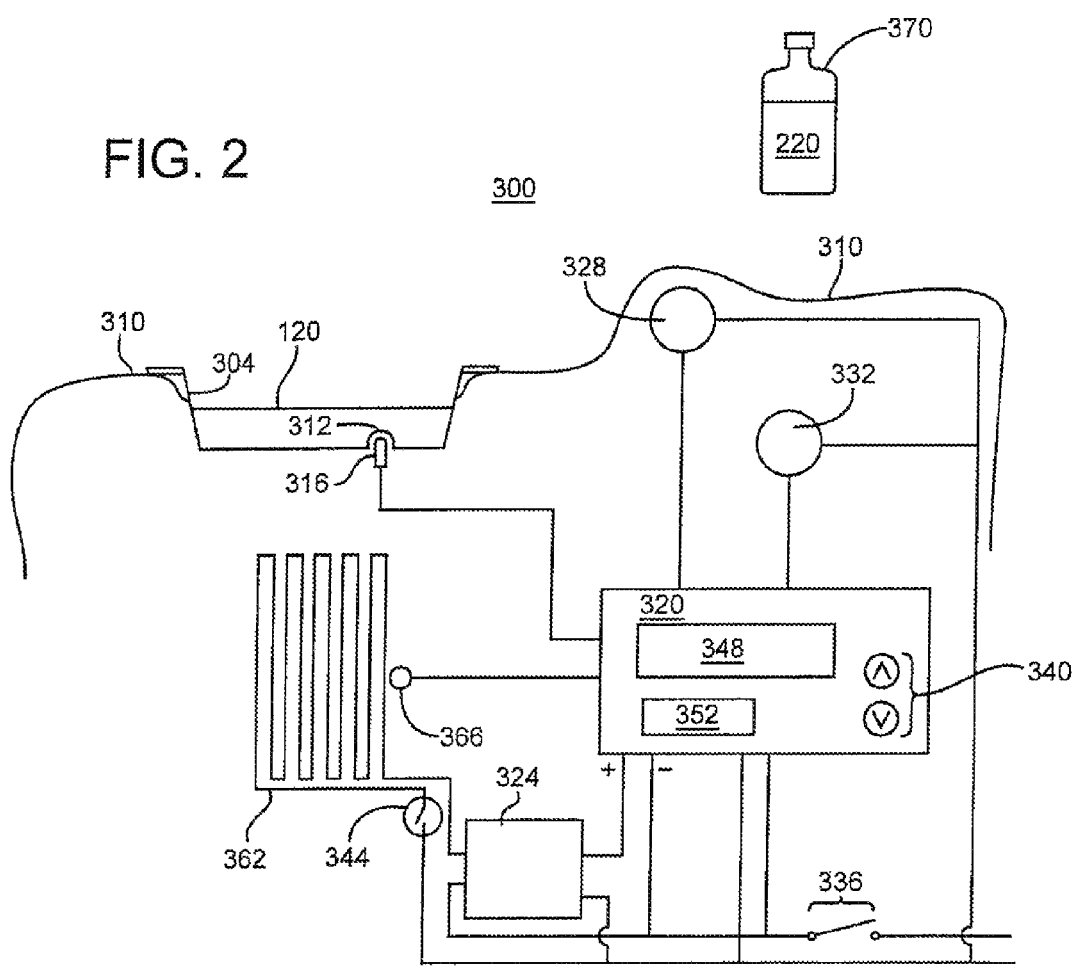
FIG. 2 illustrates the various components associated with providing a controlled amount of heat to maintain the temperature of the sterile fluid.

FIG. 2 illustrates the various components associated with providing a controlled amount of heat to maintain the temperature of the sterile fluid 120. The sterile fluid 120 is inside modified basin 304 with integral thermocouple well 312 and temperature sensor 316. The based on the input from controller 320 to relay 324 the basin heater 362 selectively applies heat that is transferred to the basin 304 and the sterile fluid 120. The controller 320 is using a dual set point control scheme based on the target temperature 352, the temperature sensed at 316 representative of the temperature of the sterile liquid 120 and the temperature measured at temperature sensor 366 representative of the temperature at the heater 362. Other control schemes may be used that may not use the temperature sensor 366.

The fluid warming device 300 has a main on/off switch 336. Some heating elements come with a mechanical thermostat 344 such as a bimetallic thermostat to provide a secondary protection against a failed control system. This second mechanical thermostat 344 acts as a switch to shut off the heater if the temperature exceeds a set temperature. This mechanical thermostat 344 should be set to a temperature that is low enough that the mechanical thermostat 344 opens before the heater 362 may overheat an empty basin 304. For example a mechanical thermostat set for 220 degrees Fahrenheit might be acceptable for use with a basin capable of withstanding permanent exposure to a 300 degree Fahrenheit heat source.

In this implementation, a modified sterile drape 310 is connected to some combination of the upper rim of the basin 304 or its outside wall so that the basin 304 extends down through the hole in the surgical drape 310. As the modified sterile drape 310 does not run along the bottom of the basin 304, the drape 310 does not interfere with the interaction of the thermocouple well 312 and the control system. Nor does the sterile drape 310 get between the bottom of the basin 304 and the heat coming from heater 362 to the bottom of the basin. The drape basin combination would typically be combined together as part of preparing a surgical kit and the drape would encircle the basin bottom with the remainder of the drape folded or pooled in the cavity of the basin so that the basin may be placed into the fluid warming device and once properly positioned, the drape may be unfolded from the basin to cover the top and upper sides of the fluid warming device to maintain a sterile field.

The interaction between the sterile drape 310 and the removable basin 304 may be a simple interference fit such that the basin once inserted into a hole in the drape stretches the drape so that the drape stays attached to the basin sufficiently for it to maintain the sterile field. Alternatively, the drape may be bonded to the outer wall of the basin or to the underside of the rim of the basin.

FIG. 2 shows drape 310 extending downward to cover the components in FIG. 2. This is illustrative of the point that the drape is used to maintain the sterile field, but one of skill in the art will recognize that individual components shown in FIG. 2 are apt to be inside a housing and not in direct contact with the drape. One exception is the tops of the indicator lamps 328 and 332 (discussed below) that must remain visible through the drape as discussed in detail below. Also as discussed below some controls may be placed outside of the sterile field and thus located below where the drape ends on the liquid warming device.

The user may alter a target temperature 352 for the fluid through the use of input keys 340. The term "user" refers to the end user of the device in the operating room. There may be a set of users of the device in the operating room including those working in the sterile field and those working outside of the sterile field. Medical equipment is also tested and serviced by technicians and engineers. The technicians and engineers that test and service the equipment are not users as they have access to tools, documentation, and controls that are not accessible to users.

The target temperature 352 and the current temperature of the fluid may be displayed on a display 348. The input keys 340 and the display 348 in one implementation are placed low on the housing so that these components are below the drape 310 and outside the sterile field. One of skill in the art will recognize that special window may be placed in the drape or the drape may be made of material with optical properties that allow a standard LED display to be read through the drape.

In one embodiment, two visual indicators are provided that may be seen from a distance to allow those participating in the surgery to check the temperature status of sterile fluid 120 from afar. When the At-Temperature indicator lamp 328 is lit, this conveys that the fluid temperature of sterile fluid 120 is at the target temperature or within a certain tolerance of that target temperature. In contrast, when the Out-of-Range indicator lamp 332 is lit, it indicates that the liquid warming device 300 has power and the main on/off switch 336 is turned on but the sterile fluid 120 is not within a certain tolerance of the target temperature. In one implementation, light 332 is not lit unless a limit switch indicates that a basin is present.

In this embodiment, a single Out-of-Range indicator is sufficient as the staff would typically know whether they had added cool water or hot water to the basin. In the event that the staff was not sure whether the temperature was above or below the desired range, the specific temperature may be obtained from the display 348. This gives the staff the information necessary to make an informed quantitative decision to use out-of-range fluid if the particular intended use of the out-of-range fluid would be acceptable. As noted below, one of skill in the art may appreciate that the Out-of-Range indicator may be revised to be two indicators: an above range indicator and a below range indicator.

A preferred embodiment uses a green lamp for At-Temperature and either a red lamp or most preferred, a yellow lamp for Out-of-Range. As the preferred embodiment separates the liquid warming device from the sterile field through the use of the sterile drape 310, the indicator lights selected (size, brightness, degree of protrusion from the surface) must be suitable for providing an adequate visual signal even through the drape material which for some drapes is not fully transparent. LED lights may be suitable for at least some drape materials. Ideally the light source should be of the type that projects light towards the drape as this helps make the visual indicator visible. While not preferred, the lights may be made more visible by placing a window of substantially transparent material in the drape so that when appropriately placed on the fluid warming device the window is placed over the visual indicator lights.

The portion of the indicator light assembly that comes in contact with the surgical drape may operate at a temperature that may be maintained in contact with a surgical drape for an extended period of time without damaging the surgical drape. An extended period of time would mean 24 hours of contact without damaging the drape.

One may provide further detail by using separate indicator lamps for above the temperature target range and one for below the temperature target range. Perhaps, blue for too cold and red for too hot. Likewise, one may add additional indicator lamps to distinguish between close to the target temperature range but still out of range from an indication that the current fluid temperature is further from the target temperature range. For instance an implementation may use a yellow lamp for close but not quite in range. One of skill in the art will note that flashing lights may be used to convey something different from constant lights. For example a flashing the In-Range and Out-of-Range lights might convey that the temperature is almost in-range.

Another alternative for indicator lights is to provide one light to indicate that the warming device is turned on and a second light to indicate that power is currently being applied to the heater 362. When the fluid temperature is significantly below the target temperature, the heater-on light will be lit for an extended period of time. As the temperature of the sterile fluid approaches the target temperature, the heater will be turned on and off thus causing the heater-on light to turn on and off. Contingent on the control scheme implemented to control the heater, the steady state operation of the control system to maintain the temperature of the sterile fluid 120 may be frequent switching of the heater on and off.

Optionally, the temperature of the sterile fluid may be printed along with the time or alternatively this information may be stored for printing later. In either case, a history of the temperature over time may be used in connection with other surgical records to document that the sterile fluid was at an appropriate temperature when used.

As evidenced by the details set forth above, a great deal of care and attention is devoted to measuring the temperature of the sterile fluid and maintaining the sterile fluid in a particular narrow temperature range through the controlled application of heat to the sterile removable basin 304.

The sterile fluid 120 is in the operating room to be used in a variety of irrigation, lavage, or other medical procedures. Thus, the volume of sterile fluid is depleted and must be periodically replenished. Sterile fluids for placement in basins for use in medical procedures typically come in plastic bottles with a substantially square cross section. Bulk storage warmers may be used to heat large quantities of such bottles to bring the sterile fluids to a particular temperature that is close to the desired temperature for a variety of procedures (such as body temperature or slightly above body temperature). These bulk warmers are typically located outside of any one surgical room so that the heated sterile fluid may be used by a several different surgically rooms. While it is convenient to have one or more un-opened bottles 370 of sterile fluid 220 placed in a surgical room in anticipation of the need to replenish the sterile fluid 120 removed from the basin, as time passes, the temperature of the heated sterile fluid 220 in the un-opened bottle 370 drops as the sterile fluid 220 cools in response to the ambient air temperature.

Replenishing the depleted supply of heated sterile fluid 120 in the basin 304 (FIG. 2) with sterile fluid 220 from the bottle 370 may cause a drop in the temperature of the sterile fluid 120 in the basin 304 to the extent where the temperature of the sterile fluid 120 in the basin 304 is no longer in the desired narrow temperature range. At this point, the medical staff is faced with the choice of waiting until the heater 362 acts to heat the volume of sterile fluid 120 back to within the desired narrow temperature ranger or use sterile fluid that is cooler than desired.

Alternatively, although probably less frequently, it is possible that a bottle 370 of sterile fluid 220 obtained from the common bulk heater may be at a temperature that is above that desired for this particular procedure so that adding this sterile fluid 220 brings the temperature of the sterile fluid 120 in the basin 304 above the desired narrow temperature range. Again the medical staff would need to choose between a delay in the procedure, using sterile fluid 120 from the basin 304 that is above the desired temperature, or perhaps finding a bottle of sterile fluid that has not yet been placed in the common bulk heater and using this cool water to quickly drop the temperature of the sterile fluid 120 in the basin 304.

Thus, it may be useful to have the ability to place one or more bottles 370 of sterile fluid 220 in a local warming unit so that bottles may be maintained or conditioned to be within or close to the desired narrow temperature range around a set point 352 so that mixing of sterile fluid 220 to replenish a depleted volume of sterile fluid 120 in the basin does not move the aggregate fluid temperature out of the desired range. Note that while the contents of the bottle are sterile, the exterior of the bottle is not considered sterile and would not have to be stored within a portion of the sterile field.

Open Access Sleeve for Heated Fluid Units.

Figure 3:
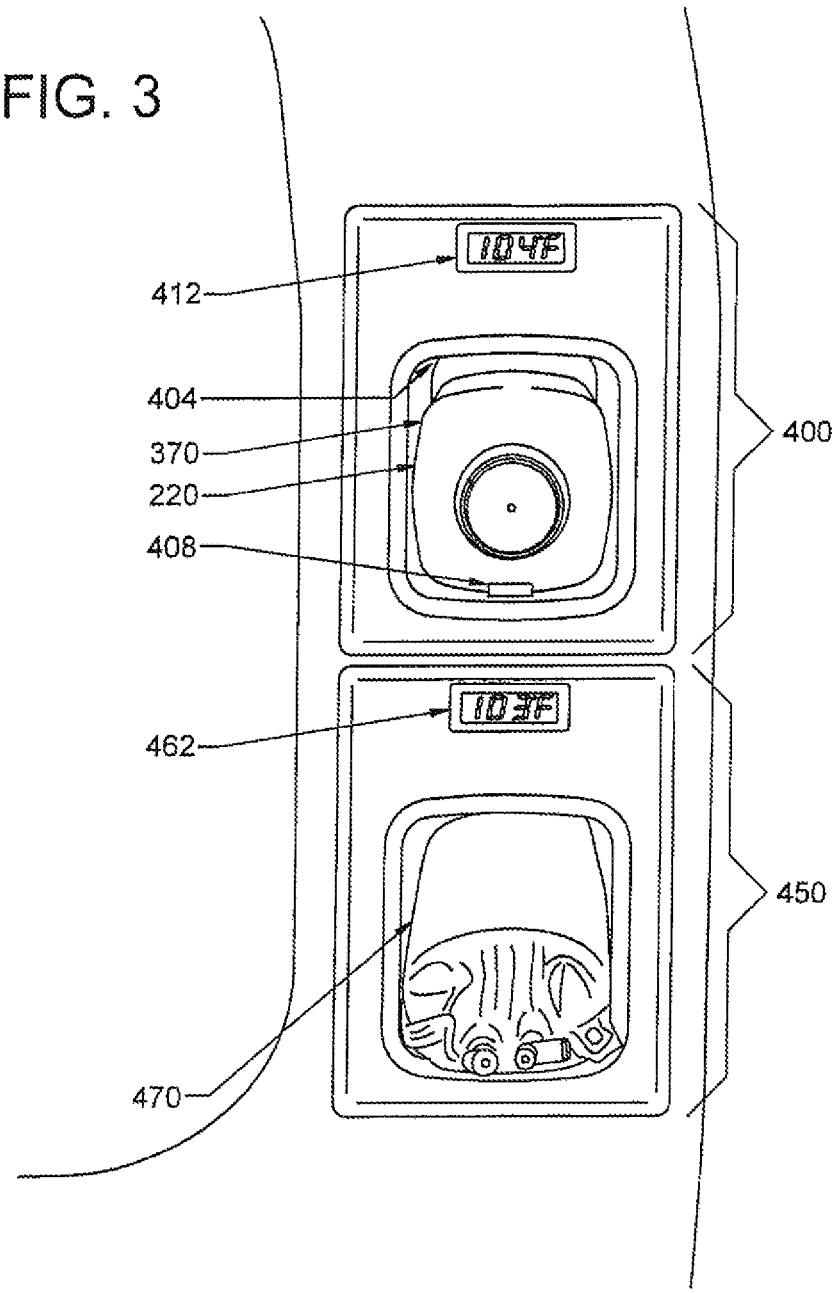
FIG. 3 illustrates an implementation in which two access sleeves 400 and 450 are provided for the local maintenance of containers of sterile fluid at a desired temperature.

FIG. 3 illustrates an implementation in which two access sleeves 400 and 450 are provided for the local maintenance of containers of sterile fluid at a desired temperature. While FIG. 3 shows an implementation with two access sleeves, the present invention may be implemented as any number of one or more access sleeves.

Bottle 370 of sterile fluid 220 is inserted into a cavity 404 in access sleeve 400. As described below, the bottom surface of the access sleeve is tilted so that the bottom front of the cavity is below the bottom rear of the cavity. A range of slopes may work for the bottom surface. The slope should be sufficient so that any liquid that is on the outside of the bottle 370 or leaks from the bottle 370 flows forward and out of the access sleeve. Thus a slope of as little as 1 degree may suffice but a slope of approximately 5 degrees or more does a better job at draining off any fluid. A protrusion 408 extends upward from near the front of the open access sleeve 400 to resist the forward movement of the bottle 370 from sliding out of the access sleeve 400. (The protrusion for access sleeve 450 is not visible as it is covered by the top portion of the IV bag of sterile fluid in that access sleeve.) The height of the protrusion 408 needed to retain the bottle 370 is primarily a function of the slope of the bottom surface of the cavity but will be influenced by the coefficient of friction between the bottle and the bottom of the cavity and the geometry of the bottle. The slope of the cavity used in this example is approximately 10 degree. Slopes up to 15 and even 20 degrees may be used with adequate protrusions.

A temperature sensor is used to detect the temperature of the bottle 370. The temperature of the bottle 370 is displayed in the temperature display 412. It is preferred to have a separate temperature sensor and display for each access sleeve. (note that the bottle 370 and the bag 470 are at slightly different temperatures as one may have come from a warmer storage cabinet than the other, or the bottle may have had more time to reach a target temperature of 104 degrees Fahrenheit than has the bag.

Access sleeve 450 has a separate temperature sensor that senses the temperature of the container placed in that access sleeve and displays that temperature in temperature display 462. To the extent that a relationship is known between the temperature measured by the temperature sensor and the average temperature of the sterile fluid in the container, a correction may be applied to the measured temperature such that the corrected temperature is displayed. For example, it may be that a temperature sensor measuring the temperature between the heated bottom wall of the access sleeve and the wall of the container may be warmer than the precise temperature of the sterile fluid as a portion of the container is in contact with ambient air at the open end of the access sleeve.

As shown in FIG. 3, medical staff may find it convenient to place a bag of sterile fluid that will be used in a manner other than emptied into basin 108 (See FIG. 1). For example the contents of the bag of sterile fluid may be introduced by a gravity based IV.

A preferred placement for the temperature sensor is on the bottom surface of the cavity. To the extent that a common brand of bottled surgical fluid has a deep concavity (including a circumferential ridge) that would impede good contact between the temperature sensor and the bottle, the distance between the temperature sensor and the protrusion may be adjusted so that a portion of the bottle that is relatively flat would be positioned over the temperature sensor. Having a significant slope to the bottom surface of the cavity helps ensure that the bottle slides forward to make contact with the protrusion so that the bottle assumes a repeatable position in the access sleeve. The temperature of the exterior of the container is used as a proxy for the temperature of the sterile fluid in the container. This assumption is not perfect as the temperature of the container surface on the bottom wall of the heated cavity may be slightly warmer than the average temperature of the fluid in the container while the fluid is being heated but should eventually be close as the fluid reaches its target temperature.

Figure 4:
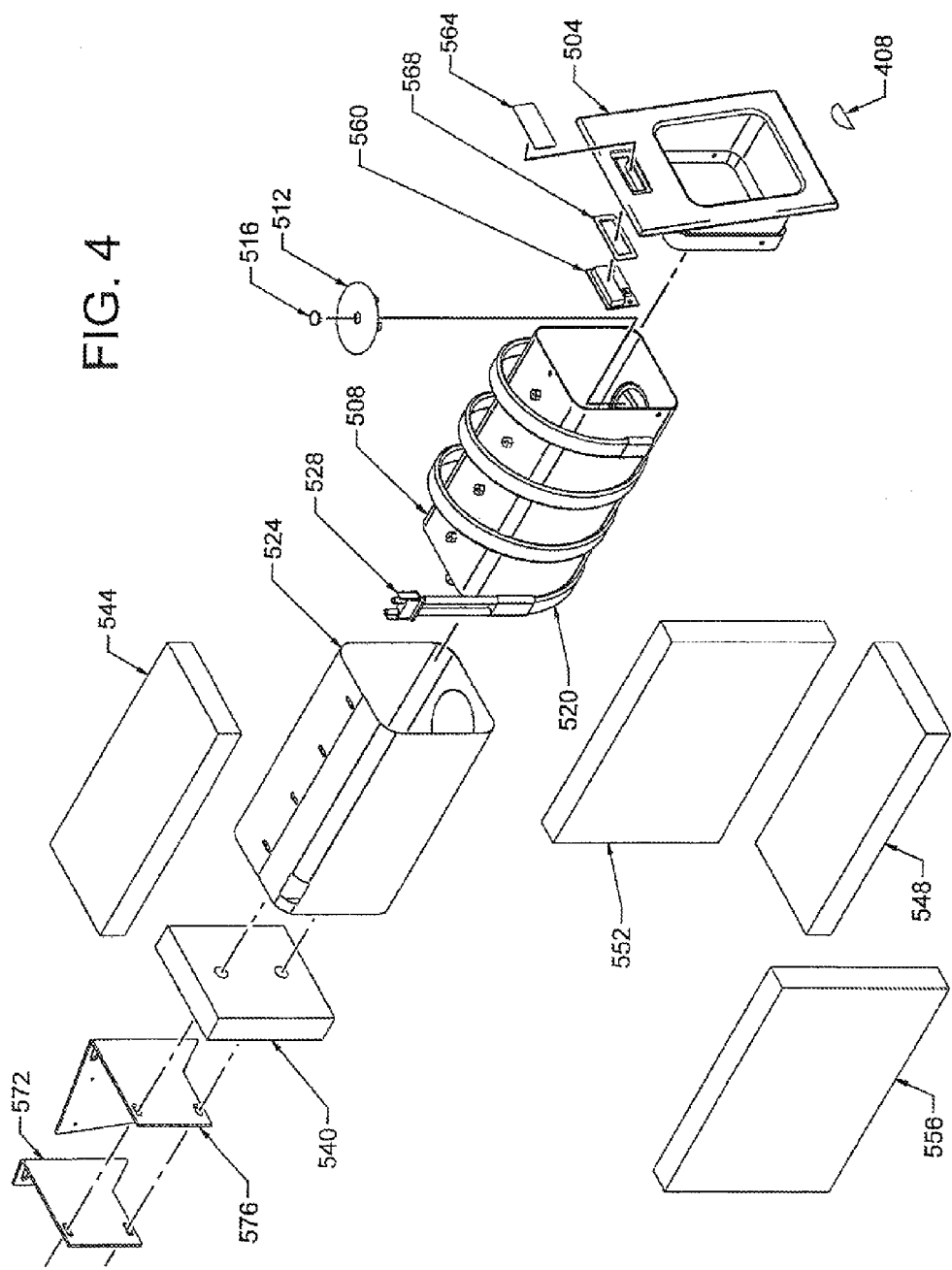
FIG. 4 is an exploded diagram of components from the access sleeve 400 shown in FIG. 3.

FIG. 4 is an exploded diagram of components from the access sleeve 400 shown in FIG. 3. Protrusion 408 may be affixed to the access sleeve face 504. The access sleeve cavity is defined in part by perimeter container 508 that receives temperature sensor insulator 512 and finishing plug 516. Perimeter container 508 in this example fits into the back of the access sleeve face 504 and may be affixed by connectors (not shown) that connect the sides and top of the perimeter container 508 to the back of the access sleeve face 504. The temperature sensor insulator 512 is intended to isolate the finishing plug 516 and the temperature sensor (not shown) from the temperature of the access sleeve perimeter container 508 so that the temperature sensor responds to the temperature of the container of sterile fluid.

Finishing plug 516 is ideally made of metal or another good thermal conductor to allow the thermistor placed in contact with the underside of the finishing plug 516 to sense the temperature of the container in contact with the top of the finishing plug 516. One of skill in the art will recognize that the thermistor or another temperature sensing device may adapted to be positioned to make contact with the container directly rather than through a finishing plug.

In this example, heat cable assembly 520 forms a helix around the perimeter container 508 and is enclosed within shield 524. The heat cable assembly 520 is connected to power at connector 528. The example shown in FIGS. 3 and 4 uses approximately six feet of 10/watt per foot self-regulating heater cable (described below).

The access sleeve is insulated by rear insulator 540, top insulator 544, bottom insulator 548, right side insulator 552, and left side insulator 556. The temperature display 412 is composed of display 560 and lens 564 affixed by adhesive frame 568. The rear insulator 540 may be connected to either short bracket 572 or long bracket 576 depending on whether it will be the lower or upper access sleeve. The specific geometry of these brackets are not central to the present invention. One of skill in the art will be able to provide an appropriate bracket to connect the access sleeve to connection points in the device.

While more sophisticated control schemes may be employed to control the operation of the heat cable assembly 520, a sufficient and cost effective control scheme is to provide power to the heat cable assembly 520 whenever the temperature sensor senses a temperature two degrees below the set point for the access sleeve. When sensing that the temperature is two degrees below the set point, full power is applied to the heat cable for that access sleeve until the temperature reaches the set point at which time power is no longer applied to the heat cable. Each heat cable is independently controlled based on the temperature reported from the temperature detector in the sleeve.

Heat cables are available that provide decreased heat output per linear foot of heat cable based on the temperature of the heat cable. One example is Nelson™ Type LT Self Regulating Heater Cable available from Nelson Heat Tracing Systems of Tulsa Okla. (www.nelsonheaters.com).

Figure 5:
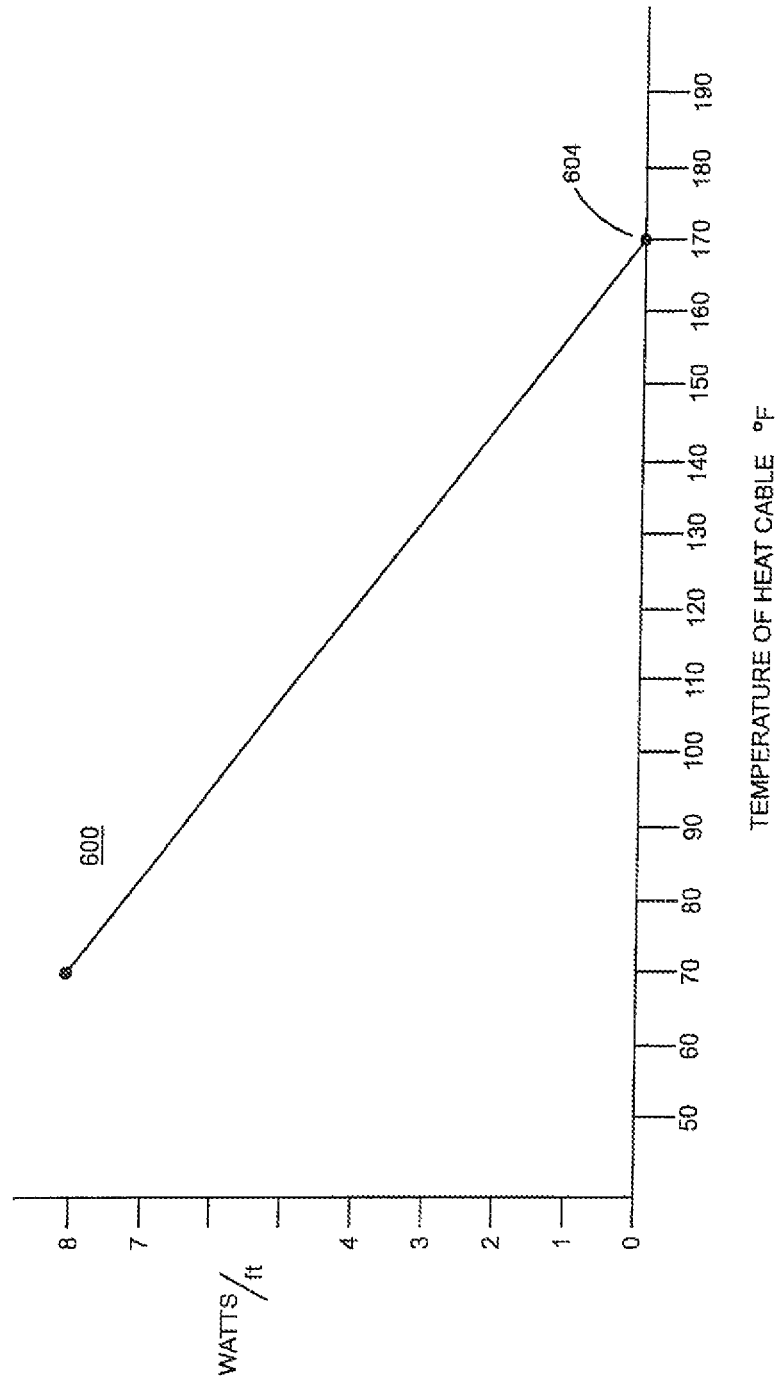
FIG. 5 is a graph of heat output as a function of temperature for an illustrative example of heat cable.

Using a heat cable makes the heating system is effectively self-regulating and make is unnecessary to have an secondary thermostat to remove power from the heat cable in the event of a failure of the control system. This type of heat cable varies the heat about based on the local temperature of the heat cable so the system compensates to resist the creation of hot spots as the cable in a section that is better insulated or having a more dense allocation of heat cable will provide less heat per foot than another section of heat cable facing cooler operating conditions. An example of the heat output as a function of temperature is shown in FIG. 5. Response curve 600 shows the decrease in watt output per linear foot of heat cable as the temperature of the heat cable increases. The response curve 600 intersects zero watts per linear foot at point 604 E indicating that the heat cables are incapable of providing additional heat as the heat cables reach approximately 170 degrees Fahrenheit. Thus, the temperature of the access sleeve cannot exceed 170 degrees even if the thermal sensor or control system should fail. At 70 degrees Fahrenheit, which is approximately the ambient temperature of an operating suite, the heater cable assembly depicted in FIG. 5 would produce approximately 8 watts/linear foot to quickly heat the access sleeve.

Ideally, the power supply is adequate to allow simultaneous operation of the heater cable assemblies for all access sleeves. While it is more efficient to not heat an empty access sleeve, the example of an access sleeve shown in FIGS. 3 and 4 do not have a container detector and the heater cable assemblies continue to heat the access sleeve.

The set point for the access sleeve temperature may be readily manipulated by the end users through input devices placed on the exterior of the device analogous to input keys 340 described in connection with input of a set point for the heated basin. The set point for the temperature setting for the access sleeves may also be adjusted through a variety of means known in the art including but not limited to varying the position of a rheostat, providing a program instruction to the control system through a data connection, dip switch settings, or the replacement of a Read Only Memory. These manipulations would not be made by end users of the heated sterile fluid but by engineers and technicians with responsibility for testing, calibrating, and servicing the equipment.

The temperature detector used in the example shown in FIGS. 3 and 4 is a thermistor. A wide range of temperature detection devices may be employed by one of skill in the art including such options as thermocouples and RTD. Thermistors provide high sensitivity, good transient response and are relatively inexpensive. This combination of features makes thermistors well suited for this application.

Alternative Embodiments

While the illustrative example provided above was useful in conveying aspects of the present invention, the illustrative example is by no means the only way to benefit from the teachings of the present application.

Alternative Heating Patterns.

FIG. 4 illustrates the use of a helical pattern for the heating element such that the heating element is in proximity to all the walls between the back wall and the open front of the access sleeve. Others may choose to apply heat to only the bottom wall or to some other subset of walls between the back wall and the open front. The back wall may be heated as well. If a heating pattern is selected that does not place heating elements in proximity to the temperature detector, then it becomes less important that the temperature detector is thermally insulated from the thermally conductive wall as a heating element that is not near the temperature detector is less likely to impact the measurement of the thermal detector even if the thermal detector is not isolated from the thermally conductive wall of the access sleeve.

The one or more heating elements used to apply thermal energy to the walls of the access sleeve do not need to be in direct contact with the walls. In order to promote effective transfer of heat between the one or more heating elements and the walls, each heating element may be placed in thermal contact at least a portion of the set of walls by providing a thermally conductive path (that is at least one path devoid of a significant thermal insulator) between heating element and the wall.

Another heating strategy that may be employed isolates one of the walls from the other walls defining the access sleeve using a thermal insulator of adequate thickness to substantially isolate the isolated walls from the adjacent walls. In this strategy, the isolated wall is not placed in thermal contact with a heating element but a temperature detector is placed in thermal contact with the isolated wall. The isolated wall is created to be a thermal conductor so that the temperature of the sterile fluid is available to the temperature detector through the container of the sterile fluid when a container of sterile fluid is placed in direct or indirect thermal contact with the isolated wall.

Alternative Protrusions.

The example set forth above uses one protrusion in the center of the access sleeve. One of ordinary skill in the art will recognize that a set of two or more protrusions may be used or that a lip from one side of the sleeve opening to another may be used. As the example set forth above anticipates that any excess fluid will flow out of the opening of the access sleeve based on the slope of the bottom of the access sleeve, the choice of protrusions should not prevent the flow of water out of the access sleeve. One of skill in the art will recognize that there are many options for achieving the dual objectives of retaining the container of sterile fluid against the pull of gravity and allowing fluids to drain out of the access sleeve. The one or more protrusion may have fenestrations to allow the flow of water through the protrusion wall or the protrusions may be angled slightly so that fluids may run along the base of the protrusion and still flow downward towards the opening in the access sleeve.

A gutter indentation behind the one or more protrusions may be connected to a drain hole that leads to either an internal container or to the floor. However, a drain passage may be deemed undesirable by some designers as adding an internal drain adds another cost to the construction of the device and may be blocked by debris lodged in the interior of the drain passage.

Configurations without Slopes to Drain to the Front of the Sleeve.

The examples given above include a discussion of an advantage from having a slope running from the back of the sleeve cavity to the front of the open sleeve so that any fluids that may be on the exterior of the container or that leak from the container flow to the front of the sleeve and out of the sleeve. While this is advantageous for some applications, the invention is not limited to this configuration.

Figure 6A:
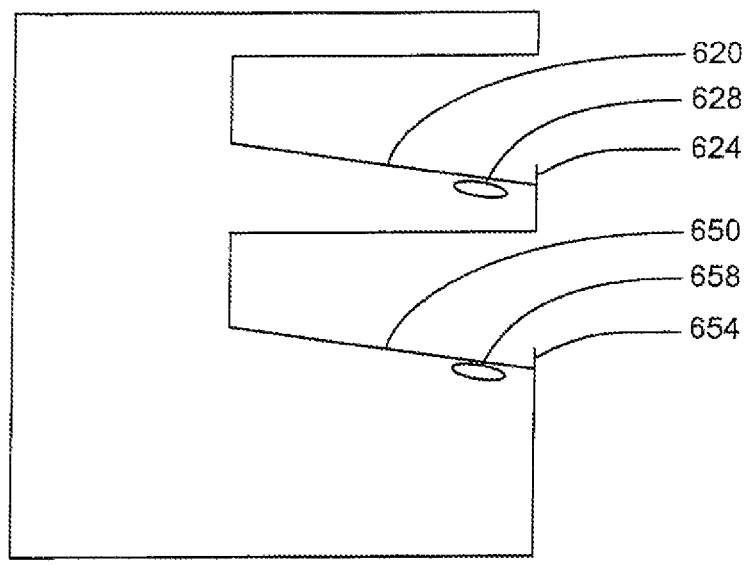
FIGS. 6A, 6B and 6C illustrate various configurations of devices including heat access sleeves with a variety of slopes towards the open end of the access sleeve.

FIG. 6 illustrates various configurations that while not exhaustive, point out the range of possible arrangements for heating containers of sterile fluid. The goal is to discuss the placement of the components relevant to this particular discussion. FIG. 6 does not show all the relevant components that are discussed in other figures of this application. FIG. 6A illustrated the concept of having two downwardly sloping sleeves represented here by sleeve bottoms 620 and 650. Near the front of the sleeves are protrusions 624 and 654. As the containers that are to be placed in these sleeves may vary in length, the temperature sensors 628 and 658 are located in the half of the sleeve closer to the front of the open sleeve.

Figure 6B:
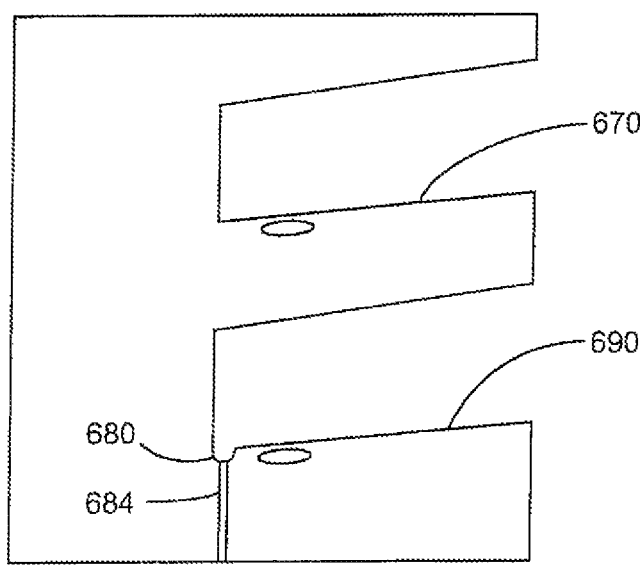

FIG. 6B shows sleeve bottoms 670 and 690 sloping away from the open front towards the closed back of the sleeve. As the slope is away from the open front, protrusions are not needed to retain the closed containers. As the length of the containers that may be placed in the sleeves may vary, it may be advantageous to place the temperature sensors towards the back of the sleeve. Optionally, a drain gutter 680 sloped to a drain hole 684 may be added in the back of the heated sleeve.

Figure 6C:
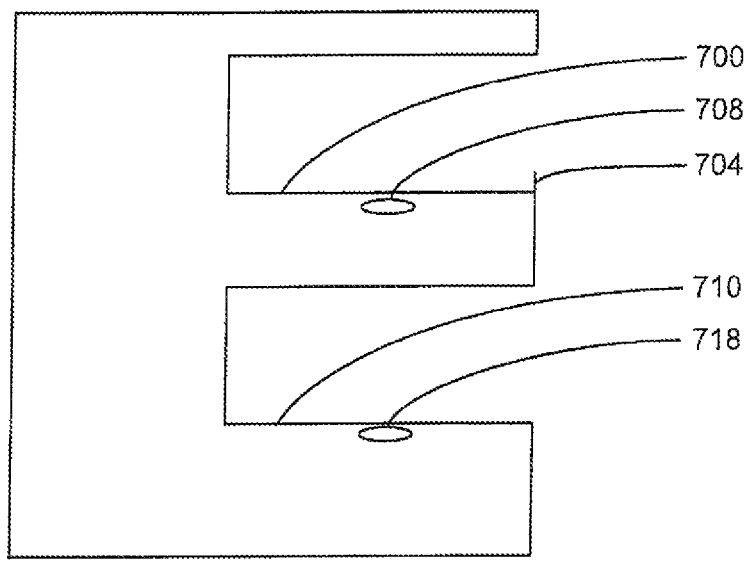

FIG. 6C represents a cross section taken through the relevant portion of the device so that the access sleeves may be seen. More specifically, FIG. 6(*c*) shows a pair of sleeve bottoms 700 and 710 that are essentially flat between the front opening of the sleeve and the closed back. A protrusion 704 may be added to help retain containers of sterile fluid while the unit is moved from place to place as the unit containing the sleeves may be mounted on wheels. Temperature sensor 708 and 718 may be placed towards the middle of the length of sleeve bottoms 700 and 710 as the position of a container in the horizontal sleeve may be either toward the front of the sleeve or towards the closed back of the sleeve.

Dual-Ended Access Sleeves.

Figure 7:
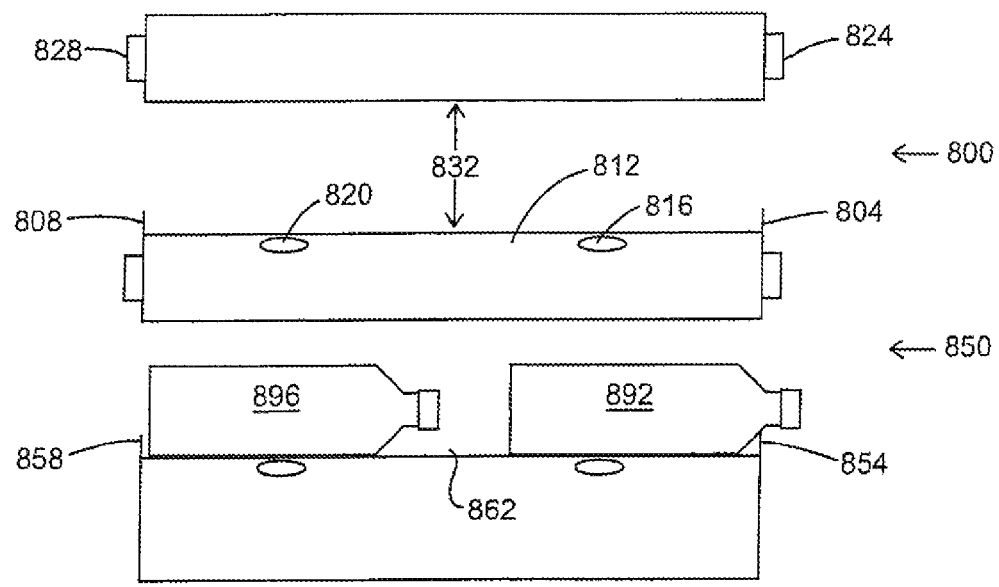
FIG. 7 illustrates a cross section of the relevant portion of an implementation of a device to expose two access sleeves 800 and 850.

FIG. 7 illustrates a cross section of the relevant portion of the device to expose two access sleeves 800 and 850. These access sleeves do not have a back wall as they continue from one end of the device to the other. Optionally, these access sleeves may have protrusions 804, 808, 854, and 858 since it is possible that the act of placing the container of sterile fluid 896 in one end of dual-ended access sleeve 850 may include pushing against previously inserted container of sterile fluid 892 until container of sterile fluid 892 stops against protrusion 854.

Optionally, the sleeve floor 812 or 862 may be essentially horizontal. While a dual-ended access sleeve may be sized so that it accommodates one, two, or more containers of sterile fluid (such as bottles shown here), many designers will find that selecting a length appropriate for two containers is a desirable choice. If adopted for maintaining two containers per sleeve, then one option for implementing the present invention is to effectively have two separate access sleeves joined where the closed back of the access sleeve would otherwise be. In such a situation, the temperature sensor 816 may provide a temperature reading that is displayed on temperature indicator 824 and used as an input in regulating the application of heat on that portion of the dual-ended access sleeve. Likewise, temperature sensor 820 provides a temperature reading displayed on temperature indicator 828 and the sensed temperature is used as in input in regulating the application of heat on that portion of the dual-ended access sleeve. Optionally, a portion of the sleeve may not be heated by either the heater regulated by temperature measured at temperature sensor 816 or by a heater regulated by the temperature measured at temperature sensor 820 if it is anticipated that this middle portion of the dual access heater sleeve will not normally have a container of sterile fluid positioned there.

Figure 8:
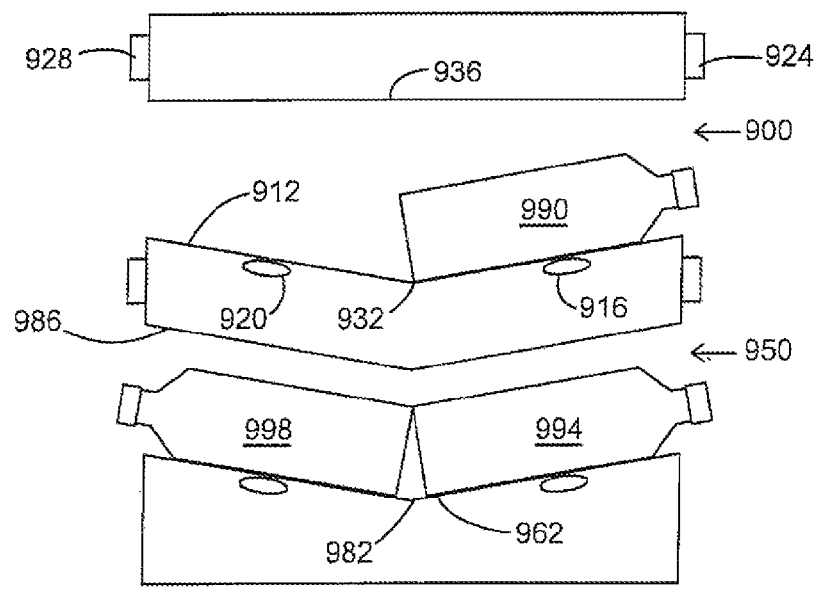
FIG. 8 shows a pair of dual-ended access sleeves 900 and 950 with sloped sleeve bottoms 912 and 962.

FIG. 8 shows a pair of dual-ended access sleeves 900 and 950 with sloped sleeve bottoms 912 and 962. The lowest points 932 and 982 of the sloped sleeve bottoms is somewhere between the two open ends to the dual-ended access sleeves 900 and 950. As with the dual-ended access sleeve shown in FIG. 7, the sleeve may be created to accommodate two bottles of sterile fluid (such as 990, 994, and 998) (or two containers of some other type).

With sloped sleeve bottoms 912 and 962, the containers will tend to move towards the low points 932 and 982. The actual position of the container may vary slightly depending on whether the dual-ended access sleeve is currently holding one or two containers. Thus, container 990 has slid further into dual-ended access sleeve 900 than has container 994 in dual-ended access sleeve 950 as dual-ended access sleeve 950 has a second container 998.

The temperature sensor 916 may be used to provide the temperature displayed in temperature indicator 924 and as an input to a controller operating the heating element providing heat to the end of the dual-ended access sleeve having temperature sensor 916. Likewise, temperature sensor 920 may be used to provide the temperature displayed in temperature indicator 928 and used as an input to a controller operating the heating element providing heat to the end of the dual-ended access sleeve having temperature sensor 920.

Dual-ended access sleeve 950 differs from dual-ended access sleeve 900 in that sleeve ceiling 986 has a downward slope and sleeve ceiling 936 is substantially horizontal. One of skill in the art may appreciate that if the ceiling contained a portion of the heating system, then sleeve ceiling 986 would place the portion of the heating system ceiling closer the container 994 and 998, than is the case with ceiling 936 and container 990. Even if the ceiling did not have a portion of the heating system, some designers may prefer to reduce the volume of air in the dual access heater sleeve by sloping the ceiling.

While not shown here, one of skill in the art may appreciate that two access sleeves with sloped bottoms running from the interior of the device to the access sleeve opening may be positioned contiguous to one another so as to form a dual-ended access sleeve with a high point in the interior of the device rather than a low point as shown in FIG. 8.

While not shown here, one of skill in the art may appreciate that two access sleeves may be positioned with essentially one downward slope from the upper opening to a second lower opening. In this implementation, containers placed into the upper opening are gravity fed towards the lower opening and may be retained by one or more protrusions extending from near the lower opening. If two or more temperature sensors are used they may be placed along the access sleeve based on the length of the primary container type anticipated for use in that access sleeve.

Access Sleeves for Substantially Vertical Storage of Containers.

The examples provided above have shown the containers of sterile fluid, such as bottles or bags, to be substantially horizontal. An advantage of such an orientation is that the opening of the access sleeve is small relative to the overall size of the container, which makes it easier to keep the container warm.

Figure 9:
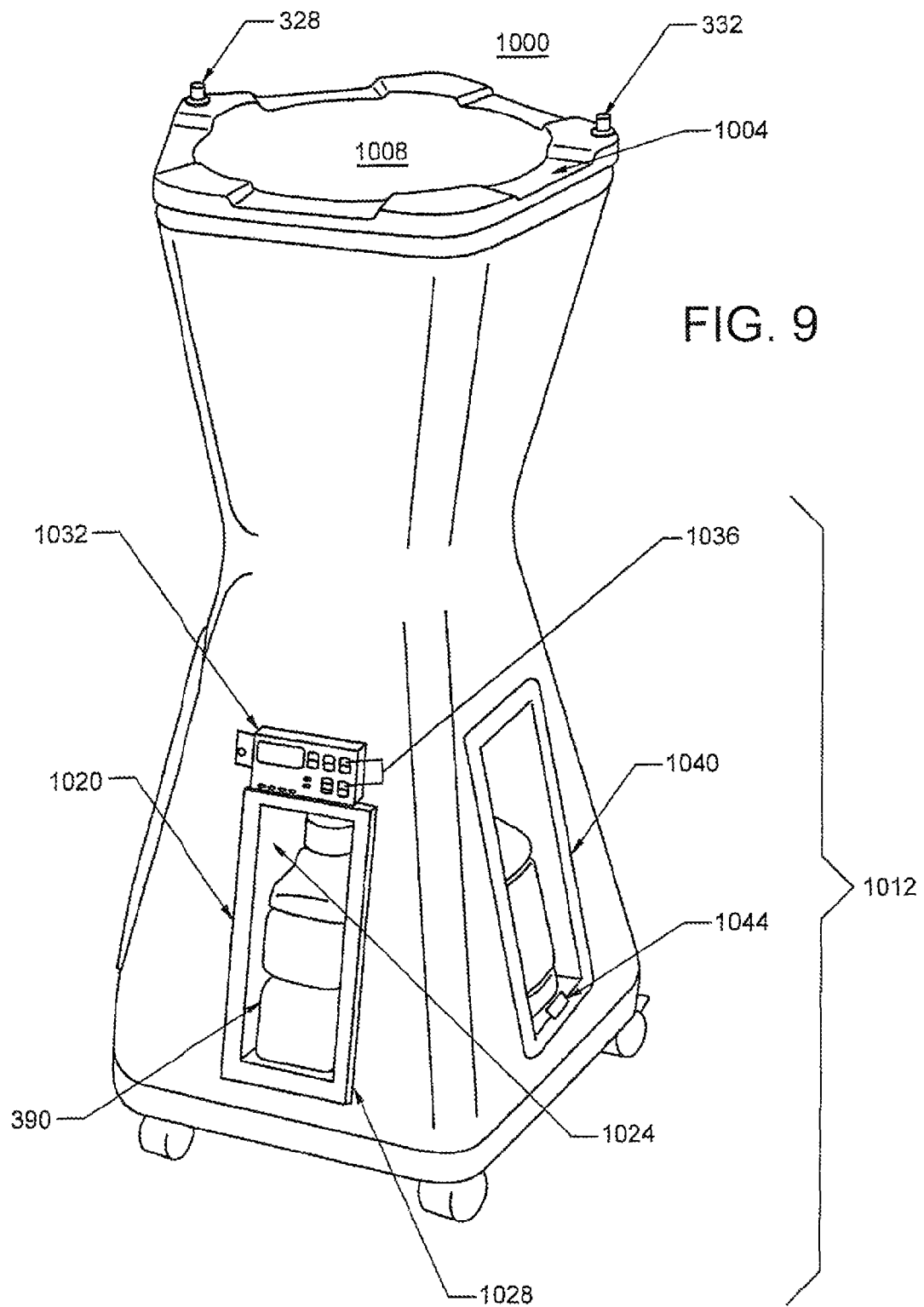
FIG. 9 is a perspective view of a device having access sleeves that are intended to maintain containers of sterile fluid in a substantially upright orientation.

An alternative type of access sleeve is shown in FIG. 9. In FIG. 9, liquid warming device 1000 has a top surface 1004 adapted to receive a sterile removable basin (not shown) in a basin cavity 1008. The sterile removable basin may be placed through a corresponding opening in a drape (not shown) so that the combination of the sterile basin and the drape form a barrier between the sterile field and the upper surfaces of the liquid warming device. Indicator lights 328 and 332 may interact with the control system to provide the user a visual indication whether temperature sensor (not shown) located beneath the sterile removable basin indicates that the sterile fluid is within a desired range of temperatures. As noted above, the set of indicator lights may be done in a variety of ways and may involve more than two indicator lights. (One may also use just a single indicator light, perhaps using patterns of flashing lights, to provide an indication of whether the temperature sensor is sensing temperatures that indicate that the sterile fluid is within a specified range of temperatures.) The indicator lights 328 and 332 are adapted so that they may be viewed through the sterile drape. Alternatively, the sterile drape may have low opacity or transparent windows that overlay the indicator lights 328 and 332.

Liquid warming device 1000 has a pentagonal top and a pentagonal base 1012. The pentagonal base 1012 has one access sleeve per pentagonal side on three sides of the liquid warming device 1000. Access sleeves 1020 and 1040 are visible from this view and a portion of the access sleeve on an adjacent face is visible as well. The two sides not visible in this view have access panels for assembly and maintenance. Access sleeve 1020 has a set of walls 1024 forming a defined perimeter and a back wall to define the cavity of the access sleeve 1020. The perimeter walls have an integrated frame 1028 that rests against the exterior wall of the liquid warming device pentagonal base 1012. The container of sterile fluid 390 fits within the cavity of the access sleeve 1000. The bottom of the sterile container 390 rests on the bottom face of the access sleeve that may be sloped towards the center of the liquid warming device so that the container of sterile fluid rests against the back wall of the access sleeve 1020. If the slope of the bottom face of the access sleeve is not discernibly sloped downward towards the centerline of the liquid warming device 1000, then some users may prefer that the liquid warming device have one or more protrusions 1044 for each access sleeve to help retain the container of sterile fluid 390 as the liquid warming device 1000 is moved or bumped.

The liquid warming device 1000 was built without temperature sensors associated with the individual access sleeves. Rather than an active control system with a feedback loop, this device uses a simpler solution that is the constant application of a small amount of heat to each of the access sleeves. Containers of sterile fluid taken from bulk heating cabinets and placed into mildly heated access sleeves cool down at a much slower rate than bottles placed on an unheated countertop. The amount of heat delivered to the access sleeves may be adjusted by controls inside the device so that the heat applied to an access sleeve with a container of sterile fluid does not get heated above the upper range of the desired temperature range for the sterile fluid, even when the ambient temperature is at the upper range of the allowable temperatures. Thus if the operating room is normally operated at 70 degrees but the operating room is qualified for operation up to 80 degrees, then the heater (or heaters) for the access wells is adjusted so that a bottle containing sterile fluid at the upper range of desired temperatures (for example 104 degrees Fahrenheit) will not increase in temperature even when the heat is applied for an extended period of time in a 80 degree room.

Liquid warming device 1000 has temperature indicator 348 and input keys 340 for monitoring the temperature obtained from the temperature indicator located near basin cavity 1008 and for changing the set point for the target range for the temperature of the sterile fluid placed in the basin that is placed in the basin cavity 1008. The temperature indicator 348 and input keys 340 are placed down adjacent to access sleeve 1020 so they are below the bottom edge of the sterile drape and thus may be seen and accessed while the drape is in place.

An alternative to a passive control system where the heaters for the vertical access sleeves are always on but may be inadequate to bring the sterile fluid to the desired temperature if the ambient air temperature is not unusually warm, is to provide an active control system for each access sleeve. Under this mode of operation, each access sleeve (such as 1020 and 1040) has a temperature sensor (not shown) that interacts with a controller (not shown) to regulate a heater (not shown) to attempt to bring the temperature sensed by that particular temperature sensor within a specific temperature range. The invention may be implemented with each access sleeve controlled by a separate controller or implemented with two or more of the access sleeves controlled by the same controller.

As the precise temperature of the containers of sterile liquid is not as important as the temperature of the sterile liquid in the sterile removable basin, some designers may choose to configure the liquid warming device 1000 so that individual temperatures obtained from the temperature sensors associated with each access sleeve are not externally displayed. Further, while the target temperature for the access sleeves may be adjusted by calibration settings inside the liquid warming device, the end user in the surgical room is not provided with an input means to adjust the target temperature for either the individual access sleeves or the access sleeves as a group.

A Device with Access Sleeves but not a Heated Basin.

Figure 10:
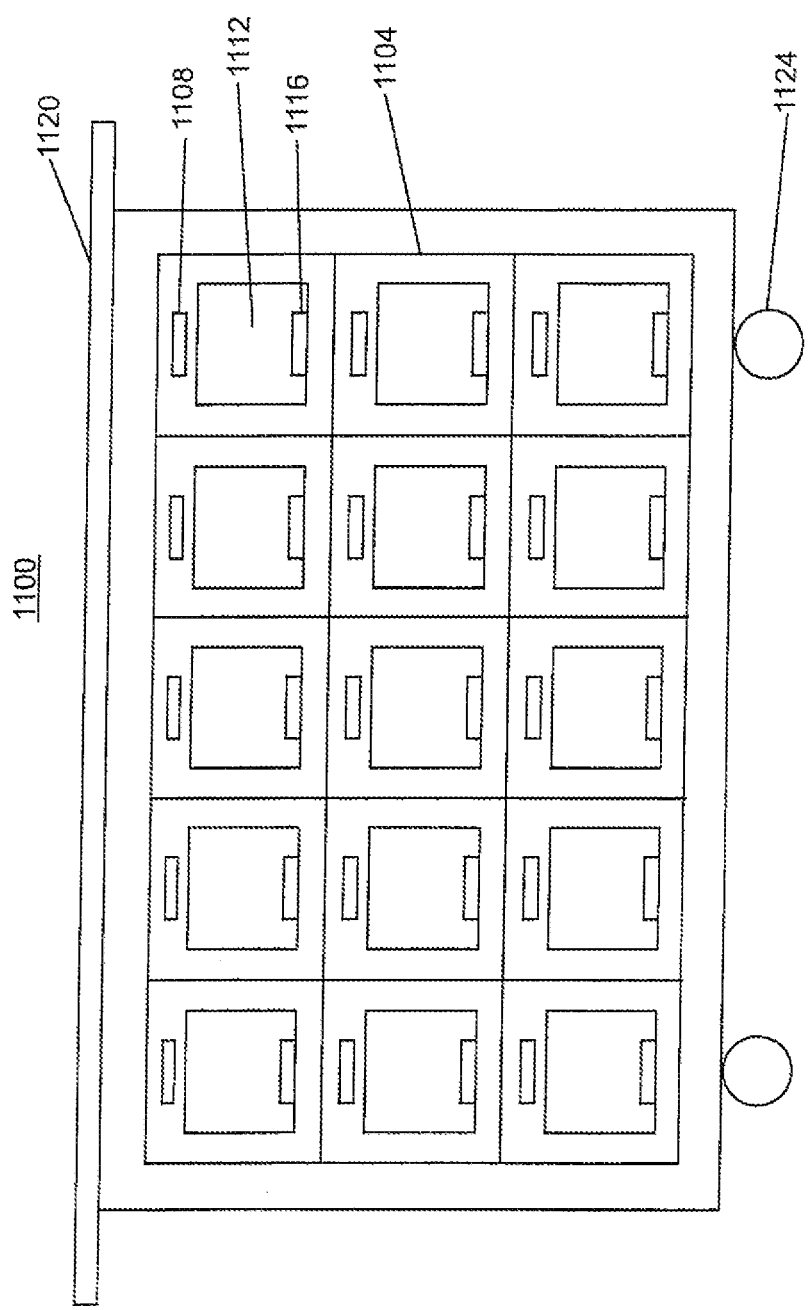
FIG. 10 shows access sleeve cabinet 1100.

The examples discussed above have included a cavity for receiving a removable basin and a heating system to heat sterile fluid place in the removable basin. The advantages of having containers of sterile fluid maintained at desired temperatures in the operating room may be obtained through use of a access sleeve cabinet having a set of access sleeves. FIG. 10 shows access sleeve cabinet 1100 with thirty access sleeves 1104. Fifteen access sleeves are visible in FIG. 10 and another fifteen access sleeves are on the opposite side of the access sleeve cabinet 1100. Each access sleeve cavity 1112 is of sufficient size to receive a bottle of sterile fluid. In this particular example, the access sleeve bottoms are tilted towards the open side of the access sleeve and thus these access sleeves have protrusions 1116. Each access sleeve has a temperature sensor (not shown) that obtains a temperature that is displayed on a corresponding temperature display 1108. The temperature is used as an input for the control system regulating temperature of that access sleeve 1104. A countertop 1120 may be placed on the access sleeve cabinet 1100 to provide a work surface outside of the sterile field. Optionally, the access sleeve cabinet may include caster type wheels to allow the cabinet to be repositioned within the operating suite or to be wheeled over to a bulk heater cabinet to restock the rolling access sleeve cabinet 1100.

Alternative Control System.

Figure 11:
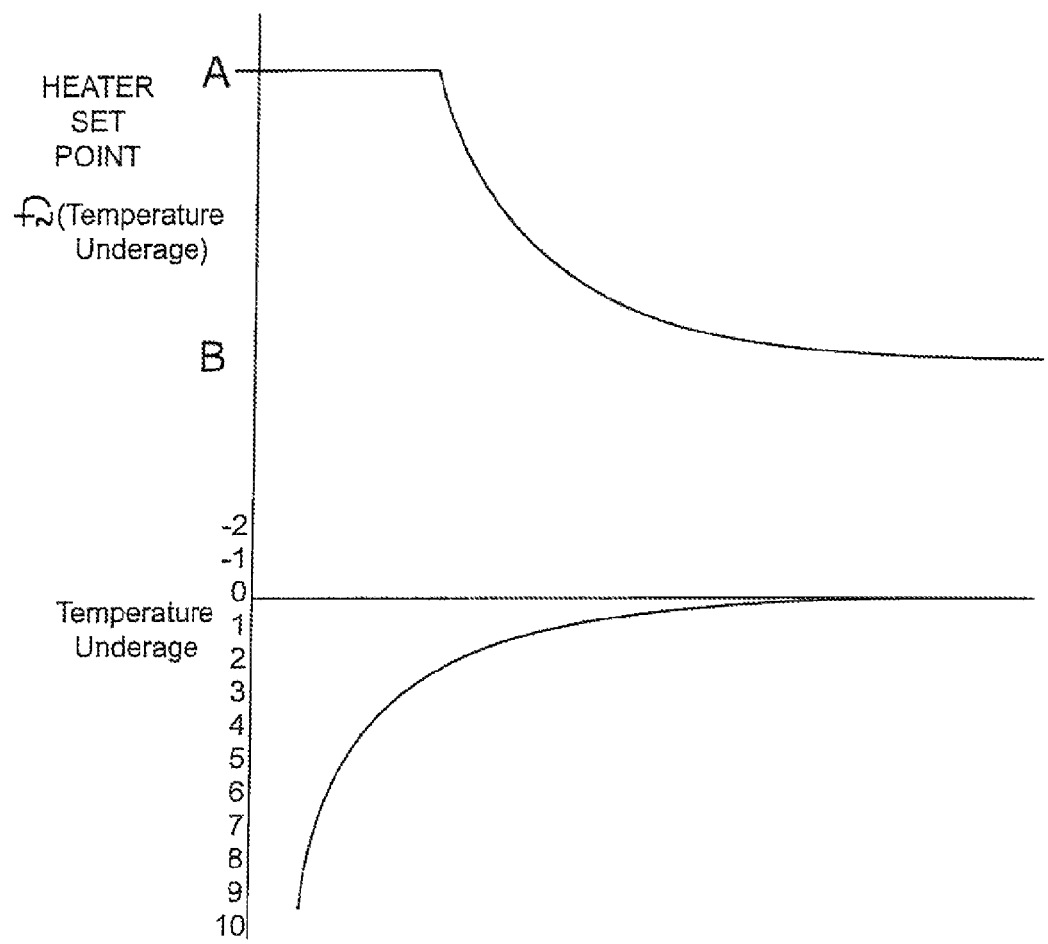
FIG. 11 is a graph to explain a cascade control scheme for controlling the application of heat.

An alternative to the combination of heater cable assembly and control system disclosed above is to use a cascade control scheme as illustrated in FIG. 11. A heater is used with excess capacity such that the heater is controlled by applying only a percentage of full power to the heater. The control system responds to the current temperature underage. The temperature underage is the difference between the target temperature and the current temperature of the sterile fluid. If the target temperature is set to 100 degrees Fahrenheit then a current temperature of 90 degrees Fahrenheit for the container of sterile fluid would indicate a 10 degree temperature underage. Advantageously, the target temperature may be modified by input keys or by other means, perhaps not by the individual users in the surgical suite but by those charged with the duty of calibrating and maintaining the equipment.

The fluid temperature controller is set to operate the heater at a maximum temperature shown on FIG. 11 as temperature A. Choosing a relatively high temperature for temperature A quickly reduce the temperature underage. However, it is prudent to choose a maximum temperature that is well below the temperature that would damage the anticipated types of containers of sterile fluid. Another factor that goes into the selection of the maximum temperature is seeking to avoid a safety risk to the personnel using the access sleeves.

The steady state temperature shown as B on FIG. 11 is not a programmed number but is the temperature of the heater that maintains the container of the sterile fluid at the desired target temperature. The temperature needed to maintain the container of sterile fluid at a set point near 100 degrees Fahrenheit will be slightly higher in an operating suite with a lower ambient air temperature than in a similarly situated operating suite with a higher ambient air temperature. In order to optimize responsiveness of the system, the maximum temperature is used as the set point for the heater until the temperature of the container of sterile fluid is relatively close to the target temperature. For example, the maximum temperature may be used until the temperature underage is only 2 degrees Fahrenheit.

As the temperature of the container of sterile fluid approaches the target temperature, the set point for the heater is reduced thus slowing the rate of temperature increase of the sterile fluid. A suitable means for controlling the heater set point is the use of a standard PID (Proportional Integral Derivative) controller. An example of a suitable PID controller is a Series 988 Controller manufactured by Watlow of Winona, Minn., www.watlow.com/products/controllers.

As the controller seeks to reduce the output of the heater, the controller operates a relay to reduce the percentage of time that the heater receives power. Thus, a heater maintaining a container of sterile fluid at the desired fluid temperature would be provided with power a smaller percentage of the time compared with the same heater bringing the same container of fluid to the desired temperature as the latter is operating at a higher set point temperature and the below temperature container of sterile fluid absorbs heat more readily.

Another implementation may remove the ability to adjust the target temperature and would essentially have a fixed target temperature. In such a case, the heater set point would become a function of the temperature of the container of sterile fluid as there would be a consistent relationship between temperature of the container of sterile fluid and the temperature underage.

Alternative to Temperature Displays.

The temperature displays such as temperature displays 412 and 462 in FIG. 3 are one example of a means of providing feedback on the temperature of the container of sterile fluid in the access sleeve. Other options exist including systems of two or more indicator lights as described above in connection with the heated basin.

Convection Based System.

The example given above uses a temperature sensor with a thermally conductive covering that contacts the side of the container of sterile fluid. An alternative is to measure the air temperature in the cavity of the access sleeve away from the open end of the access sleeve. This temperature will be influenced by the temperature of the container of sterile fluid and eventually the temperature of the air and the temperature of the container of fluid will converge. Such as system would allow two or more containers of fluid to be placed in the access sleeve and the system may use convection rather than contact heat to convey heat to the cavity and any containers held in the cavity of the access sleeve.

Liquid Heating Devices not Using the Basin/Drape Combination Referenced Above.

Some of the examples given above have identified a basin holding sterile fluid that is kept warm by a heater. The basin is placed into a basin cavity through an opening in a sterile drape so that the basin and the drape form a protective barrier to isolate the sterile field from the device. While this is advantageous, it is not required for use of the inventive teachings with respect to access sleeves. One may place the sterile fluid directly into a cavity in the top of the device if the cavity and the top of the device were adequately sterilized for the intended use. One may place the sterile fluid in a sterile drape that forms a draped cavity inside a cavity in the top of the device. Alternatively, one may place the sterile fluid in a sterile drape in a basin in a cavity in the top of the device.

V Configuration to Access Sleeve.

While the implementations described above have used a bottom wall of the open access sleeve that was substantially horizontal in the axis running perpendicular to the front to back axis, this is not a requirement of the invention. One of ordinary skill in the art may implement an open access sleeve for heated fluid units that has a V shape or curved shape instead of a flat bottom wall.

Figure 12:
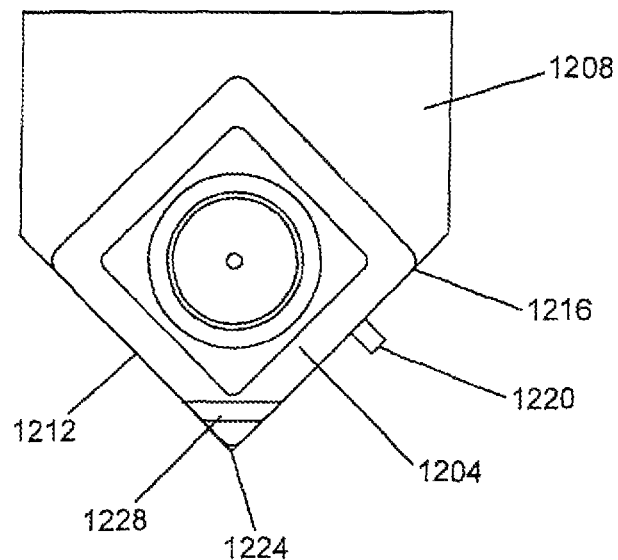
FIG. 12 shows an implementation a pair of V-shaped walls 1212 and 1216.

FIG. 12 shows an implementation that does not use a flat bottom wall. A bottle of fluid 1204 is placed inside access sleeve 1208 with a pair of V-shaped walls 1212 and 1216 that support the bottle of fluid 1204. The bottle of fluid 1204 may be made of material that allows the weight of the fluid to partially conform the shape of the bottle to the shape of the v-shaped walls. A temperature sensor 1220 may be placed adjacent to an opening in one of the pair of V-shaped walls and insulated from the wall so that when the bottle of fluid 1204 is placed in thermal contact with the temperature sensor 1220, the temperature detected by the temperature sensor 1220 may be used as an input to a control system to regulate a set of one or more heaters applying heat to the access sleeve.

The slope of the centerline 1224 between the pair of V-shaped walls 1212 and 1216 may be sloped towards the open end of the access sleeve to promote drainage of fluids and to cause the bottle to tend to rest against one or more protrusions. The protrusions may protrude from one or both of the pair if V-shaped walls. The protrusion may be arranged to extend from one of the walls to the other as shown with retainer protrusion 1228.

An implementation using a pair of V-shaped walls where the centerline is substantially horizontal from the front to the back of the access sleeve or slopes downward towards the back of the access sleeve may be implemented without a protrusion in the front of the access sleeve.

Figure 13:
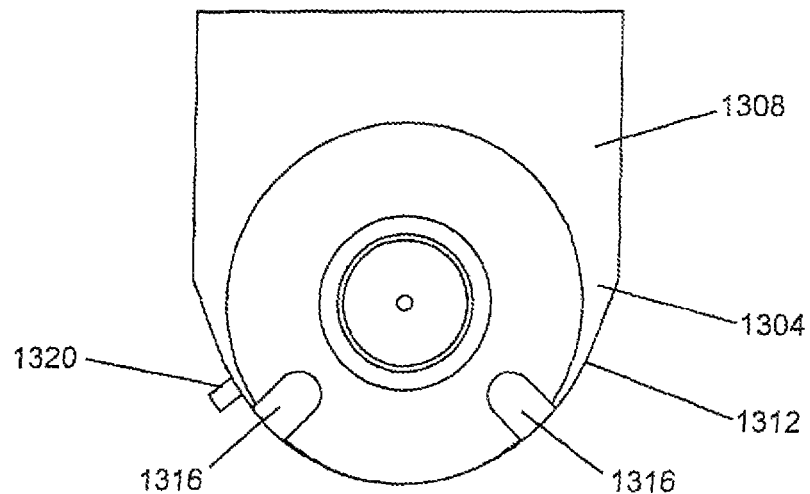
FIG. 13 is a front view of an access sleeve having a bottom surface with an arc that is similar to the radius of bottles used in the access sleeve.

The access sleeve may be implemented with other wall configurations that substantially correspond to the shape of a portion of the primary container used in the access sleeve. FIG. 13 is a front view of an access sleeve 1308 having a bottom surface 1312 with an arc that is similar to the radius of bottles 1304 used in the access sleeve. A temperature sensor 1320 may be placed adjacent to an opening in the bottom surface 1312 so that when the bottle 1304 is placed in thermal contact with the temperature sensor 1320, the temperature obtained by the temperature sensor 1320 may be used as an input to a control system to regulate a set of one or more heaters applying heat to the access sleeve. An implementation using a curved bottom wall may be sloped towards the open front of the access sleeve and the bottle retained by one or more protrusions 1316. The bottom may be substantially horizontal along the axis from the open front to the closed back of the access sleeve or may have a downward slope that leads away from the open front of the access sleeve.

One or skill in the art will recognize that the alternative embodiments set forth above are not mutually exclusive and that in some cases alternative embodiments may be created that implement two or more of the variations set forth above. For example, a dual-ended access sleeve may be implemented with a pair of V-shaped walls and use convection heating even though that specific combination of features was not described above, but rather the individual features were introduced by discussion of specific illustrative implementations.

Section headers have been used to break up long stretches of text in order to make it easier to find material relating to certain topics. These section headers are merely aids and do not impose limitations on the interpretation of text found after that section heading.

Those skilled in the art will recognize that the methods and apparatus of the present invention have many applications and that the present invention is not limited to the specific examples given to promote understanding of the present invention. Moreover, the scope of the present invention covers the range of variations, modifications, and substitutions for the system components described herein, as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority that granted this patent such as the United States Patent and Trademark Office or its counterpart.

What is claimed is:

1. A method of slowing the cooling of sterile fluid in a closed container of sterile fluid from an initial temperature T1 to the ambient temperature of a room containing the closed container of sterile fluid, the method comprising:
   connecting a device having at least one access sleeve to a power source to provide electric power to at least one heater to heat at least a portion of the walls surrounding an access sleeve; and
   placing the closed container of sterile fluid in the access sleeve with at least one side of the access sleeve remaining open to ambient air;
   wherein the access sleeve slows the cooling of the sterile fluid in the closed container from the initial temperature T1 towards the ambient temperature of the room containing the closed container.

2. The method of slowing the cooling of sterile fluid of claim 1 further including adjusting at least one internal setting within the device to alter the behavior of the at least one heater.

3. The method of slowing the cooling of sterile fluid of claim 1 wherein the at least one heater operates without temperature feedback from a temperature sensor.

4. The method of slowing the cooling of sterile fluid of claim 1 wherein the at least one heater operates in response to a control system that receives a temperature measurement from a temperature sensor associated with the access sleeve.

5. The method of slowing the cooling of sterile fluid of claim 1 wherein the at least one heater operates in response to a control system that receives a temperature measurement from a temperature sensor in contact with a wall of the access sleeve.

6. The method of slowing the cooling of sterile fluid of claim 1 wherein the at least one heater operates in response to a control system that receives a temperature measurement from a temperature sensor in contact with the closed container of sterile fluid placed in the access sleeve.

7. The method of slowing the cooling of sterile fluid of claim 1 wherein the at least one heater operates in response to a control system that receives a temperature measurement from a temperature sensor in contact with air inside the access sleeve.

8. The method of slowing the cooling of sterile fluid of claim 1 wherein a controller response to a temperature input controls the at least one heater to avoid heating the closed container of sterile fluid above a target temperature.

* * * * *